United States Patent
Patient (10) Patent No.: US 10,738,044 B2
(45) Date of Patent: Aug. 11, 2020

(54) THERAPEUTIC COMPOUND AND USE IN THERAPY

(71) Applicant: PROXIMAGEN, LLC, Plymouth, MN (US)

(72) Inventor: Lee Patient, Cambridge (GB)

(73) Assignee: PROXIMAGEN, LLC, Plymouth, MN (US)

( * ) Notice: Subject to any disclaimer, the term of this patent is extended or adjusted under 35 U.S.C. 154(b) by 0 days.

(21) Appl. No.: 15/745,947

(22) PCT Filed: Jul. 21, 2016

(86) PCT No.: PCT/GB2016/052214
§ 371 (c)(1),
(2) Date: Jan. 18, 2018

(87) PCT Pub. No.: WO2017/017414
PCT Pub. Date: Feb. 2, 2017

(65) Prior Publication Data
US 2019/0185467 A1    Jun. 20, 2019

(30) Foreign Application Priority Data

Jul. 24, 2015 (GB) .................................. 1513115.4

(51) Int. Cl.
*A61K 31/44* (2006.01)
*C07D 471/04* (2006.01)
(Continued)

(52) U.S. Cl.
CPC .............. *C07D 471/04* (2013.01); *A61P 1/00* (2018.01); *A61P 1/16* (2018.01); *A61P 9/00* (2018.01);
(Continued)

(58) Field of Classification Search
CPC .......... C07D 471/06; A61P 25/00; A61P 9/00; A61P 1/16; A61P 1/00; A61P 19/02; A61P 21/00; A61K 31/44
(Continued)

(56) References Cited

U.S. PATENT DOCUMENTS

2011/0207746 A1    8/2011   Savory et al.
2012/0302583 A1    11/2012  Savory et al.
(Continued)

FOREIGN PATENT DOCUMENTS

WO    2007/146188    12/2007
WO    2010/031789    3/2010

OTHER PUBLICATIONS

Lewinsohn, "Mammalian Monoamine-Oxidizing Enzymes, With Special Reference to Benzylamine Oxidase in Human Tissues", *Brazilian J. Med. Biol. Res.*, vol. 17, pp. 223-256, 1984.
(Continued)

*Primary Examiner* — Taylor V Oh
(74) *Attorney, Agent, or Firm* — Greenblum & Bernstein, P.L.C.

(57) ABSTRACT

{4-[3-(Dimethylamino)propoxy]phenyl}methyl (4S)-4-(propan-2-yl)-3H,4H,5H,6H,7H-imidazo[4,5-c]pyridine-5-
(Continued)

EFFECT OF THERAPEUTIC TREATMENT OF EXAMPLE 1 ON ARTHRITIC INDEX
IN THE MOUSE COLLAGEN-INDUCED ARTHRITIS MODEL

DATA POINTS REPRESENT MEAN ± S.E.M. ALL ANIMALS SURVIVING AT EACH TIME POINT ARE INCLUDED. N=10/GROUP AT THE START. N=9 AFTER DAY 4 IN EXAMPLE 1 (50mg/kg) GROUP; N=8 AFTER DAY 3 IN EXAMPLE 1 (100mg/kg) GROUP

TREATMENTS (po)

**P<0.01 ONE-WAY ANOVA FOLLOWED BY DUNNETT'S MULTIPLE COMPARISON TEST VS VEHICLE. ALL ANIMALS SURVIVING ON DAY 14 INCLUDED (n=8-10/GROUP)

carboxylate, and pharmaceutically or veterinarily acceptable salts thereof.

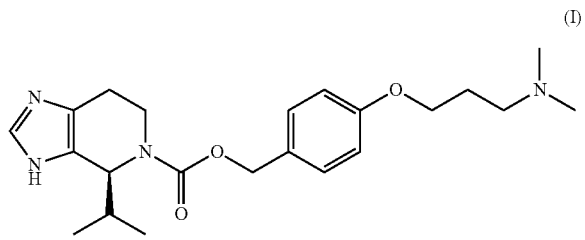

(I)

3 Claims, 7 Drawing Sheets (51) Int. Cl.
*A61P 21/00* (2006.01)
*A61P 1/16* (2006.01)
*A61P 9/00* (2006.01)
*A61P 19/02* (2006.01)
*A61P 1/00* (2006.01)
*A61P 25/00* (2006.01)

(52) U.S. Cl.
CPC .............. *A61P 19/02* (2018.01); *A61P 21/00* (2018.01); *A61P 25/00* (2018.01)

(58) Field of Classification Search
USPC .......................................................... 514/303
See application file for complete search history.

(56) References Cited

U.S. PATENT DOCUMENTS

2014/0121219 A1 5/2014 Savory et al.
2015/0218161 A1 8/2015 Savory et al.

OTHER PUBLICATIONS

Yu et al., "Characterization of Human Serum and Umbilical Artery Semicarbazide-Sensitive Amine Oxidase (SSAO)", *Biochemical Pharmacology*, vol. 47, No. 6, pp. 1055-1059, 1994.
Nakos et al., "Light Microscopic Visualization of Semicarbazide-Sensitive Amine Oxidase (Benzylamine Oxidase) Using a Cerium Method", *Folia Histochemica et Cytobiologica*, vol. 32, No. 1, pp. 3-10, 1994.
Jaakkola et al., "Human Vascular Adhesion Protein-1 in Smooth Muscle Cells", *American Journal of Pathology*, vol. 155, pp. 1953-1965, 1999.
Lyles et al., "Properties and Functions of Tissue-bound Semicarbazide-Sensitive Amine Oxidases in Isolated Cell Preparations and Cell Cultures", *J. Neural. Transm. Suppl.*, vol. 52, pp. 239-250, 1998.
Salmi et al., "VAP-1: An Adhesin and An Enzyme", *TRENDS in Immunology*, vol. 22, pp. 211-216, 2001.
Morin et al., "Semicarbazide-Sensitive Amine Oxidase Substrates Stimulate Glucose Transport and Inhibit Lipolysis in Human Adipocytes", *The Journal of Phamacology and Experimental Therapeutics*, vol. 297, pp. 563-572, 2001.
Kurkijärvi et al., "Circulating Form of Human Vascular Adhesion Protein-1 (VAP-1): Increased Serum Levels in Inflammatory Liver Diseases", *J. Immunol*, vol. 161, pp. 1549-1557, 1998.
Enrique-Tarancón et al., "Role of Semicarbazide-Sensitive Amine Oxidase on Glucose Transport and GLUT4 Recruitment to the Cell Surface in Adipose Cells", *J. Biol. Chem.*, vol. 273, pp. 8025-8032, 1998.
Fontana et al., "Amine Oxidase Substrates Mimic Several of the Insulin Effects on Adipocyte Differentiation in 3T3 F442A Cells", *Biochem. J.*, vol. 356, pp. 769-777, 2001.
Mercier et al., "Semicarbazide-Sensitive Amine Oxidase Activation Promotes Adipose Conversion of 3T3-L1 cells", *Biochem. J.*, vol. 358, pp. 335-342, 2001.
Salmi et al., "Vascular Adhesion Protein-1 (VAP-1)", *Adhesion Molecules: Function and Inhibition*, edited by Klaus Ley, pp. 237-251, 2007.
Langford et al., "Semicarbazide-Sensitive Amine Oxidase and Extracellular Matrix Deposition by Smooth-Muscle Cells", *Cardiovascular Toxicology*, vol. 2, pp. 141-150, 2002.
Göktürk et al., "Overexpression of Semicarbazide-Sensitive Amine Oxidase in Smooth Muscle Cells Leads to an Abnormal Structure of the Aortic Elastic Laminas", *Am J. Pathol.*, vol. 163, No. 5, pp. 1921-1928, 2003.
Noda et al., "Vascular Adhesion Protein-1 Blockade Suppresses Choroidal Neovascularization", *FASEB J.*, vol. 22, pp. 2928-2935, 2008.
Ekblom, "Potential Therapeutic Value of Drugs Inhibiting Semicarbazide-Sensitive Amine Oxidase: Vascular Cytoprotection in Diabetes Mellitus ", *Pharmacological Research*, vol. 37, No. 2, pp. 87-92, 1998.
Boomsma et al., "Plasma Semicarbazide-Sensitive Amine Oxidase is Elevated in Patients with Congestive Heart Failure", *Cardovascular Research*, vol. 33, pp. 387-391, 1997.
Boomsma et al., "Circulating Semicarbazide-Sensitive Amine Oxidase is Raised Both in Type I (Insulin-Dependent), in Type II (Non-Insulin-Dependent) Diabetes Mellitus and Even in Childhood Type I Diabetes at First Clinical Diagnosis", *Diabetologia*, vol. 42, pp. 233-237, 1999.
Mészáros et al., " Determination of Human Serum Semicarbazide-Sensitive Amine Oxidase Activity: A Possible Clinical Marker of Atherosclerosis", *European Journal of Drug and Metabolism and Pharmacokinetics*, vol. 24, No. 4, pp. 299-302, 1999.
Yu et al., "Physiological and Pathological Implications of Semicarbazide-Sensitive Amine Oxidase.", *Biochim. Biophys. Acta*, vol. 1647, pp. 193-199, 2003.
Mátyus et al., "Semicarbazide-Sensitive Amine Oxidase: Current Status and Perspectives", *Current Medicinal Chemistry*, vol. 11, pp. 1285-1298, 2004.
Del Mar Hernandez et al., "Human Plasma Semicarbazide Sensitive Amine Oxidase (SSAO), β-Amyloid Protein and Aging", *Neuroscience Letters*, vol. 384, pp. 183-187, 2005.
O'Sullivan et al., "Semicarbazide-Sensitive Amine Oxidases: Enzymes with Quite a Lot to Do", *NeuroToxicology*, vol. 25, pp. 303-315, 2004.
Callingham et al., "Some Aspects of the Pathophysiology of Semicarbazide-Sensitive Amine Oxidase Enzymes", *Progress in Brain Research*, vol. 106, pp. 305-321, 1995.
Jiang et al., "The Contribution of Cerebral Vascular Semicarbazide-Sensitive Amine Oxidase to Cerebral Amyloid Angiopathy in Alzheimer's Disease", *Neuropathology and Applied Neurobiology*, vol. 34, pp. 194-204, 2008.
Salter-Cid et al., "Anti-Inflammatory Effects of Inhibiting the Amine Oxidase Activity of Semicarbazide-Sensitive Amine Oxidase", *J. Pharm. Experim. Therap.*, vol. 315, No. 2, pp. 553-562, 2005.
Salmi et al., "A Cell Surface Amine Oxidase Directly Controls Lymphocyte Migration", *Immunity*, vol. 14, pp. 265-276, 2001.
O'Rourke et al., "Benefit of Inhibiting SSAO in Relapsing Experimental Autoimmune Encephalomyelitis", *J. Neural Transm.*, vol. 114, pp. 845-849, 2007.
Kirton et al., "Function-Blocking Antibodies to Human Vascular Adhesion Protein-1: A Potential Anti-Inflammatory Therapy", *Eur. J. Immunol.*, vol. 35, pp. 3119-3130, 2005.
Stolen et al., "Absence of the Endothelial Oxidase AOC3 Leads to Abnormal Leukocyte Traffic In Vivo", *Immunity*, vol. 22, pp. 105-115, 2005.
McDonald et al., "Semicarbazide Sensitive Amine Oxidase and Vascular Adhesion Protein-1: One Protein Being Validated as a Therapeutic Target for Inflammatory Diseases", *Annual Reports in Medicinal Chemistry*, vol. 42, pp. 229-243, 2007.

(56) References Cited

OTHER PUBLICATIONS

Noda et al., "Inhibition of Vascular Adhesion Protein-1 Suppresses Endotoxin-Induced Uveitis", *FASEB J.*, vol. 22, pp. 1094-1103, 2008.
Weston et al., "Hepatic Consequences of Vascular Adhesion Protein-1 Expression", *J. Neural Transm.*, vol. 118, pp. 1055-1064, 2011.
Singh et al., "Expression of Vascular Adhesion Protein-1 in Normal and Inflamed Mice Lungs and Normal Human Lungs", *Virchows Arch.*, vol. 442, pp. 491-495, 2003.
Irjala et al., "Vascular Adhesion Protein 1 Mediates Binding of Immunotherapeutic Effector Cells to Tumor Endothelium", *J. Immunol.*, vol. 166, pp. 6937-6943, 2001.
Yoong et al., "Vascular Adhesion Protein-1 and ICAM-1 Support the Adhesion of Tumor-Infiltrating Lymphocytes to Tumor Endothelium in Human Hepatocellular Carcinoma", *J. Immunol.*, vol. 160, pp. 3978-3988, 1998.
Marttila-Ichihara et al., "Small-Molecule Inhibitors of Vascular Adhesion Protein-1 Reduce the Accumulation of Myeloid Cells into Tumors and Attenuate Tumor Growth in Mice", *J. Immunol.*, vol. 184, pp. 3164-3173, 2010.
International Search Report issued in PCT/GB2016/052214, dated Sep. 12, 2016.

THERAPEUTIC COMPOUND AND USE IN THERAPY

FIELD OF THE INVENTION

This invention relates to a new SSAO inhibitor compound, and the use of that compound in medicine, and in particular to the use of the compound in the treatment of humans and animals suffering from a condition susceptible to modulation by an SSAO inhibitor.

BACKGROUND OF THE INVENTION

Semicarbazide-sensitive amine oxidase (SSAO) activity is an enzyme activity expressed by Vascular Adhesion Protein-1 (VAP-1) or Amine Oxidase, Copper Containing 3 (AOC3), belongs to the copper-containing amine oxidase family of enzymes (EC.1.4.3.6). Therefore inhibitors of the SSAO enzyme may also modulate the biological functions of the VAP-1 protein.

SSAO activity has been found in a variety of tissues including vascular and non-vascular smooth muscle tissue, endothelium, and adipose tissue [Lewinsohn, *Braz. J. Med. Biol. Res.* 1984, 17, 223-256; Nakos & Gossrau, *Folia Histochem. Cytobiol.* 1994, 32, 3-10; Yu et al., *Biochem. Pharmacol.* 1994, 47, 1055-1059; Castillo et al., *Neurochem. Int* 1998, 33, 415-423; Lyles & Pino, *J. Neural. Transm. Suppl.* 1998, 52, 239-250; Jaakkola et al., *Am. J. Pathol.* 1999, 155, 1953-1965; Morin et al., *J. Pharmacol. Exp. Ther.* 2001, 297, 563-572; Salmi & Jalkanen, *Trends Immunot* 2001, 22, 211-216]. In addition, SSAO protein is found in blood plasma and this soluble form appears to have similar properties as the tissue-bound form [Yu et al., *Biochem. Pharmacol.* 1994, 47, 1055-1059; Kurkijärvi et al., *J. Immunol.* 1998, 161, 1549-1557].

The precise physiological role of this abundant enzyme has yet to be fully determined, but it appears that SSAO and its reaction products may have several functions in cell signalling and regulation. For example, recent findings suggest that SSAO plays a role in both GLUT4-mediated glucose uptake [Enrique-Tarancon et al., *J. Biol. Chem.* 1998, 273, 8025-8032; Morin et al., *J. Pharmacol. Exp. Ther.* 2001, 297, 563-572] and adipocyte differentiation [Fontana et al., *Biochem. J.* 2001, 356, 769-777; Mercier et al., *Biochem. J.* 2001, 358, 335-342]. In addition, SSAO has been shown to be involved in inflammatory processes where it acts as an adhesion protein for leukocytes [Salmi & Jalkanen, *Trends Immunot* 2001, 22, 211-216; Salmi & Jalkanen, in "*Adhesion Molecules: Functions and Inhibition*" K. Ley (Ed.), 2007, pp. 237-251], and might also play a role in connective tissue matrix development and maintenance [Langford et al., *Cardiovasc. Toxicol.* 2002, 2(2), 141-150; Göktürk et al., *Am. J. Pathol.* 2003, 163(5), 1921-1928]. Moreover, a link between SSAO and angiogenesis has recently been discovered [Noda et al., *FASEB J.* 2008, 22(8), 2928-2935], and based on this link it is expected that inhibitors of SSAO have an anti-angiogenic effect.

Several studies in humans have demonstrated that SSAO activity in blood plasma is elevated in conditions such as congestive heart failure, diabetes mellitus, Alzheimer's disease, and inflammation [Lewinsohn, *Braz. J. Med. Biol. Res.* 1984, 17, 223-256; Boomsma et al., *Cardiovasc. Res.* 1997, 33, 387-391; Ekblom, *Pharmacol. Res.* 1998, 37, 87-92; Kurkijärvi et al., *J. Immunol.* 1998, 161, 1549-1557; Boomsma et al., *Diabetologia* 1999, 42, 233-237; Meszaros et al., *Eur. J. Drug Metab. Pharmacokinet.* 1999, 24, 299-302; Yu et al., *Biochim. Biophys. Acta* 2003, 1647(1-2), 193-199; Mátyus et al., *Curr. Med. Chem.* 2004, 11(10), 1285-1298; O'Sullivan et al., *Neurotoxicology* 2004, 25(1-2), 303-315; del Mar Hernandez et al., *Neurosci. Lett.* 2005, 384(1-2), 183-187]. It has been suggested that reactive aldehydes and hydrogen peroxide produced by endogenous amine oxidases contribute to the progression of cardiovascular diseases, diabetic complications and Alzheimer's disease [Callingham et al., *Prog. Brain Res.* 1995, 106, 305-321; Ekblom, *Pharmacol. Res.* 1998, 37, 87-92; Yu et al., *Biochim. Biophys. Acta* 2003, 1647(1-2), 193-199; Jiang et al., *Neuropathol Appl Neurobiol.* 2008, 34(2), 194-204]. Furthermore, the enzymatic activity of SSAO is involved in the leukocyte extravasation process at sites of inflammation where SSAO has been shown to be strongly expressed on the vascular endothelium [Salmi et al., *Immunity* 2001, 14(3), 265-276; Salmi & Jalkanen, in "*Adhesion Molecules: Functions and Inhibition*" K. Ley (Ed.), 2007, pp. 237-251]. Accordingly, inhibition of SSAO has been suggested to have a therapeutic value in the prevention of diabetic complications and in inflammatory diseases [Ekblom, *Pharmacol. Res.* 1998, 37, 87-92; Salmi et al., *Immunity* 2001, 14(3), 265-276; Salter-Cid et al., *J. Pharmacol. Exp. Ther.* 2005, 315(2), 553-562].

WO2007146188 teaches that blocking SSAO activity inhibits leucocyte recruitment, reduces the inflammatory response, and is expected to be beneficial in prevention and treatment of seizures, for example, in epilepsy.

O'Rourke et al (*J Neural Transm.* 2007; 114(6):845-9) examined the potential of SSAO inhibitors in neurological diseases, having previously demonstrated the efficacy of SSAO inhibition in a rat model of stroke. An SSAO inhibitor is tested on relapsing-remitting experimental autoimmune encephalomyelitis (EAE), a mouse model that shares many characteristics with human multiple sclerosis. The data demonstrates the potential clinical benefit of small molecule anti-SSAO therapy in this model and therefore in treatment of human multiple sclerosis.

SSAO knockout animals are phenotypically overtly normal but exhibit a marked decrease in the inflammatory responses evoked in response to various inflammatory stimuli [Stolen et al., *Immunity* 2005, 22(1), 105-115]. In addition, antagonism of its function in wild type animals in multiple animal models of human disease (e.g. carrageenan-induced paw inflammation, oxazolone-induced colitis, lipopolysaccharide-induced lung inflammation, collagen-induced arthritis, endotoxin-induced uveitis) by the use of antibodies and/or small molecules has been shown to be protective in decreasing the leukocyte infiltration, reducing the severity of the disease phenotype and reducing levels of inflammatory cytokines and chemokines [Kirton et al., *Eur. J. ImmunoL* 2005, 35(11), 3119-3130; Salter-Cid et al., J. *Pharmacol. Exp. Ther.* 2005, 315(2), 553-562; McDonald et al., *Annual Reports in Medicinal Chemistry* 2007, 42, 229-243; Salmi & Jalkanen, in "*Adhesion Molecules: Functions and Inhibition*" K. Ley (Ed.), 2007, pp. 237-251; Noda et al., *FASEB J.* 2008 22(4), 1094-1103; Noda et al., *FASEB J.* 2008, 22(8), 2928-2935]. This anti-inflammatory protection seems to be afforded across a wide range of inflammatory models all with independent causative mechanisms, rather than being restricted to one particular disease or disease model. This would suggest that SSAO may be a key nodal point for the regulation of the inflammatory response, and it is therefore likely that SSAO inhibitors will be effective anti-inflammatory drugs in a wide range of human and animal diseases. VAP-1 has also been implicated in the progression and maintenance of fibrotic diseases including those of the liver and lung. Weston and Adams (J Neural Transm. 2011, 118(7), 1055-64) have summarized the experimental data implicating VAP-1 in liver fibrosis, and Weston et al (EASL Poster 2010) reported that blockade of VAP-1 accelerated the resolution of carbon tetrachloride induced fibrosis. In addition VAP-1 has been implicated in inflammation of the lung (e.g. Singh et al., 2003, Virchows Arch 442:491-495) suggesting that VAP-1 blockers would reduce lung inflammation and thus be of benefit to the treatment of cystic fibrosis by treating both the pro-fibrotic and pro-inflammatory aspects of the disease.

SSAO (VAP-1) is up regulated in gastric cancer and has been identified in the tumour vasculature of human melanoma, hepatoma and head and neck tumours (Yoong K F, McNab G, Hubscher S G, Adams D H. (1998), J Immunol 160, 3978-88.; lrjala H, Salmi M, Alanen K, Gre'nman R, Jalkanen S (2001), Immunol. 166, 6937-6943; Forster-Horvath C, Dome B, Paku S, et al. (2004), Melanoma Res. 14, 135-40.). One report (Marttila-lchihara F, Castermans K, Auvinen K, Oude Egbrink M G, Jalkanen S, Griffioen A W, Salmi M. (2010), J Immunol. 184, 3164-3173.) has shown that mice bearing enzymically inactive VAP-1 grow melanomas more slowly, and have reduced tumour blood vessel number and diameter. The reduced growth of these tumours was also reflected in the reduced (by 60-70%) infiltration of myeloid suppressor cells. Encouragingly VAP-1 deficiency had no effect on vessel or lymph formation in normal tissue.

For the above reasons, it is expected that inhibition of SSAO will reduce the levels of pro-inflammatory enzyme products (aldehydes, hydrogen peroxide and ammonia) whilst also decreasing the adhesive capacity of immune cells and correspondingly their activation and final extra-vasation. Diseases where such an activity is expected to be therapeutically beneficial include all diseases where immune cells play a prominent role in the initiation, maintenance or resolution of the pathology, such inflammatory diseases and immune/autoimmune diseases. Examples of such diseases include multiple sclerosis, arthritis and vasculitis.

An unmet medical need exists for new inhibitors of SSAO having utility in medicine, including veterinary medicine, in the treatment of humans and animals suffering from a condition susceptible to modulation by an SSAO inhibitor.

SUMMARY OF THE INVENTION

The present invention makes available the new SSAO inhibitor compound {4-[3-(Dimethylamino)propoxy]phenyl}methyl(4S)-4-(propan-2-yl)-3H,4H,5H,6H,7H-imidazo[4,5-c]pyridine-5-carboxylate, and pharmaceutically acceptable salts thereof.

The invention relates also to pharmaceutical compositions comprising {4-[3-(Dimethylamino)propoxy]phenyl}methyl (4S)-4-(propan-2-yl)-3H,4H,5H,6H,7H-imidazo[4,5-c]pyridine-5-carboxylate, and one or more pharmaceutically acceptable excipients and/or carriers.

The invention relates also to the use of {4-[3-(Dimethylamino)propoxy]phenyl}methyl (4S)-4-(propan-2-yl)-3H,4H,5H,6H,7H-imidazo[4,5-c]pyridine-5-carboxylate in medicine, including veterinary medicine.

The invention relates also to the use of {4-[3-(Dimethylamino)propoxy]phenyl}methyl (4S)-4-(propan-2-yl)-3H,4H,5H,6H,7H-imidazo[4,5-c]pyridine-5-carboxylate in the treatment of a human or an animal suffering from a disease or condition susceptible to modulation of SSAO.

In an embodiment, the disease or condition susceptible to modulation of SSAO is selected from inflammation, an inflammatory disease, an immune or an autoimmune disorder, or inhibition of tumour growth.

In an embodiment the inflammation or inflammatory disease or immune or autoimmune disorder is selected from arthritis (including rheumatoid arthritis, juvenile rheumatoid arthritis, osteoarthritis and psoriatic arthritis), synovitis, vasculitis, Sjogren's disease, a condition associated with inflammation of the bowel (including Crohn's disease, ulcerative colitis, inflammatory bowel disease and irritable bowel syndrome), atherosclerosis, multiple sclerosis, Alzheimer's disease, vascular dementia, Parkinson's disease, cerebral amyloid angiopathy, cerebral autosomal dominant arteriopathy with subcortical infarcts and leukoencephalopathy, a pulmonary inflammatory disease (including asthma, chronic obstructive pulmonary disease and acute respiratory distress syndrome), a fibrotic disease (including idiopathic pulmonary fibrosis, cardiac fibrosis, liver fibrosis and systemic sclerosis (scleroderma)), an inflammatory disease of the skin (including contact dermatitis, atopic dermatitis and psoriasis), an inflammatory disease of the eye (including age related macular degeneration, uveitis and diabetic retinopathy), systemic inflammatory response syndrome, sepsis, an inflammatory and/or autoimmune condition of the liver (including autoimmune hepatitis, primary biliary cirrhosis, alcoholic liver disease, sclerosing cholangitis, and autoimmune cholangitis), diabetes (type I or II) and/or the complications thereof, chronic heart failure, congestive heart failure, an ischemic disease (including stroke and ischemia-reperfusion injury) or myocardial infarction and/or the complications thereof, or epilepsy.

In an embodiment, {4-[3-(Dimethylamino)propoxy]phenyl}methyl (4S)-4-(propan-2-yl)-3H,4H,5H,6H,7H-imidazo[4,5-c]pyridine-5-carboxylate has utility in the treatment of an animal suffering from a disease or condition susceptible to modulation of SSAO. In an embodiment the animal is a non-human mammal. In an embodiment the animal is a companion animal. In an embodiment, the animal is selected from the group consisting of cat, dog, rodent including mouse, rabbit, gerbil, chinchilla, rat, guinea pig, hamster, horse, pony, donkey, livestock including pig, cow, bull, and sheep.

DESCRIPTION OF THE INVENTION

Compositions and Formulations

{4-[3-(Dimethylamino)propoxy]phenyl}methyl (4S)-4-(propan-2-yl)-3H,4H,5H,6H,7H-imidazo[4,5-c]pyridine-5-carboxylate may be used as such or in the form of a pharmaceutically acceptable salt. For the avoidance of doubt, the term 'pharmaceutically acceptable salt(s)' as used herein includes veterinarily acceptable salt(s); and the term 'pharmaceutical composition(s)' as used herein includes veterinary composition(s). Pharmaceutically acceptable salts include, for example, acid addition salts derived from inorganic or organic acids, such as hydrochlorides, hydrobromides, p-toluenesulphonates, methansulphonates phosphates, sulphates, perchlorates, acetates, trifluoroacetates, propionates, citrates, malonates, succinates, lactates, oxalates, tartrates and benzoates.

A typical dosage is 1 to 200 mg/kg, administered one or more times per day or by continuous infusion. The drug is preferably administered via the intravenous route, or the oral route. In an embodiment the typical dosage is 1 to 100 mg/kg orally twice a day, or 1 to 200 mg/kg orally once per day. It will be understood, however, that the specific dose level for any particular patient will depend upon a variety of factors including the age, body weight, general health, sex, diet, time of administration, drug combination and the severity of the particular condition undergoing therapy.

A pharmaceutical or veterinary composition containing the active ingredient may be in any suitable form, for example aqueous or non-aqueous solutions or suspensions, dispersible powders or granules, transdermal or transmucosal patches, creams, ointments or emulsions.

The pharmaceutical or veterinary composition may be in the form of a sterile injectable aqueous or non-aqueous (e.g. oleaginous) solution or suspension. The sterile injectable preparation may also be in a sterile injectable solution or suspension in a non-toxic parenterally-acceptable diluent or solvent, for example as a solution in 1,3-butanediol. Among the acceptable vehicles and solvents that may be employed are water, phosphate buffer solution, Ringer's solution and isotonic sodium chloride solution. In addition, sterile, fixed oils are conventionally employed as a solvent or suspending medium. For this purpose, any bland fixed oil may be employed, including synthetic mono- or diglycerides. In addition, fatty acids such as oleic acid find use in the preparation of injectables. Suspensions may be formulated according to the known art using those suitable dispersing or wetting agents and suspending agents which have been mentioned elsewhere.

Aqueous suspensions contain the active ingredient in admixture with excipients suitable for the manufacture of aqueous suspensions. Such excipients are suspending agents, for example sodium carboxymethylcellulose, methylcellulose, hydroxypropylmethylcellulose, sodium alginate, polyvinyl-pyrrolidone, gum tragacanth and gum acacia; dispersing or wetting agents such as a naturally occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such a polyoxyethylene with partial esters derived from fatty acids and hexitol anhydrides, for example polyoxyethylene sorbitan monooleate. The aqueous suspensions may also contain one or more preservatives, for example ethyl or n-propyl p-hydroxybenzoate, one or more colouring agents, one or more flavouring agents, and one or more sweetening agents, such as sucrose or saccharin.

Non-aqueous (i.e. oily) suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are known.

The pharmaceutical or veterinary compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally occurring gums, for example gum acacia or gum tragacanth, naturally occurring phosphatides, for example soya bean, lecithin, and esters or partial esters derived from fatty acids and hexitol anhydrides, for example sorbitan monooleate and condensation products of the said partial esters with ethylene oxide, for example polyoxyethylene sorbitan monooleate.

The active agent may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials include cocoa butter and polyethylene glycols.

For topical delivery, transdermal and transmucosal patches, creams, ointments, jellies, solutions or suspensions may be employed. For sub-lingual delivery, fast dissolving tablet formulations may be used, as well as a number of the presentations described above. For oral administration, the drug may be administered as tablets, capsules or liquids.

Synthesis of {4-[3-(Dimethylamino)propoxy]phenyl}methyl (4S)-4-(propan-2-yl)-3H,4H,5H,6H,7H-imidazo[4,5-c]pyridine-5-carboxylate (Example 1)

The following abbreviations have been used:
CFA Complete Freund's adjuvant
DCM Dichloromethane
DIPEA Diisopropylethylamine
DMSO Dimethylsulfoxide (−)-DPTT (−)-Di-O,O'-p-toluyl-L-tartaric acid
DSC N,N-Disuccinimidylcarbonate
ee enantiomeric excess
ES+ Electrospray
EtOAc Ethyl acetate
EtOH Ethanol
h hour
HPLC High Performance Liquid Chromatography
IUPAC International Union of Pure and Applied Chemistry
LCMS Liquid Chromatography Mass Spectrometry
LPS Lipopolysaccharide
MeCN Acetonitrile
[MH]+ Protonated molecular ion
min minute
RP Reverse phase
Rt Retention time
TFA Trifluoroacetic acid
Experimental Methods Reactions were conducted at room temperature unless otherwise specified. Preparative chromatography was performed using a CombiFlash Companion system equipped with GraceResolv silica column. Reverse Phase HPLC was performed on a Gilson system with a UV detector equipped with Phenomenex Synergi Hydro RP 150×10 mm, or YMC ODS-A 100/150×20 mm columns. The purest fractions were collected, concentrated and dried under vacuum. Compounds were typically dried in a vacuum oven at 40° C. prior to purity analysis. Compound analysis was performed by HPLC/LCMS using an Agilent 1100 HPLC system/Waters ZQ mass spectrometer connected to an Agilent 1100 HPLC system with a Phenomenex Synergi, RP-Hydro column (150×4.6 mm, 4 um, 1.5 mL per min, 30° C., gradient 5-100% MeCN (+0.085% TFA) in water (+0.1% TFA) over 7 min, 200-300 nm). Enantiomeric excesses were determined by Chiral HPLC performed on an Agilent 1200 system using an Astec Chirobiotic V 100×4.6 mm 5 um column. The compounds prepared were named using IUPAC nomenclature.

Intermediate 1

(4S)-4-(Propan-2-yl)-3H,4H,5H,6H,7H-imidazo[4,5-c]pyridine

Histamine dihydrochloride (47.7 g, 259 mmol) was suspended in EtOH (150 mL) and water (5 mL), NaOH (20.7 g, 518 mmol) was added and the reaction mixture was heated to 75° C. Isobutyraldehyde (28.6 mL, 314 mmol) was added drop-wise over 50 min and the reaction mixture was stirred at 75° C. for 18 h, cooled to 0° C. for 1 h and filtered, washing with EtOH (250 mL). The combined filtrates were diluted with EtOH (400 mL) and (−)-DPTT (200 g, 518 mmol), water (1.2 L) and EtOH (400 mL) were added. The reaction mixture was heated to 58° C. until dissolution was complete and was then allowed to cool to room temperature over 16 h. The precipitate was collected by filtration and re-crystallised three times from 1:1 EtOH:water. This process was repeated on the same scale (47.7 g) and the products were combined and re-crystallised six times from 1:1 EtOH:water at 80° C. The residue (146 g, 155 mmol) was suspended in EtOAc (285 mL) and a solution of $H_2SO_4$ (9.00 mL, 168 mmol) in water (107 mL) was added. The reaction mixture was stirred at room temperature for 1.5 h and the aqueous layer was separated, washed with EtOAc (177 mL), cooled to 0° C. and a solution of KOH (19.2 g, 342 mmol) in water (16 mL) and EtOH (73 mL) was added cautiously. The reaction mixture was diluted with EtOH (177 mL) and allowed to warm to room temperature for 72 h. The reaction mixture was filtered, washing with EtOH (100 mL) and concentrated in vacuo to give the title compound (21.0 g, 24.5%) as a light yellow oil. LCMS (ES+): 166.1 [MH]+. HPLC: Rt 0.51 min, 98.8% purity. Chiral HPLC: Rt 8.79 min, >99% ee.

Example 1

{4-[3-(Dimethylamino)propoxy]phenyl}methyl (4S)-4-(propan-2-yl)-3H,4H,5H,6H,7H-imidazo[4,5-c]pyridine-5-carboxylate {4-[3-(Dimethylamino)propoxy]phenyl}methanol (13.9 g, 66.6 mmol) was dissolved in MeCN (200 mL) and cooled to 0° C. DSC (17.1 g, 66.6 mmol) and DIPEA (11.7 mL, 90.8 mmol) were added and the reaction mixture was stirred at 0° C. for 1 h. A suspension of Intermediate 1 (10.0 g, 60.5 mmol) in DCM (100 mL) was added and the reaction mixture was stirred for 17 h and concentrated in vacuo. The residue was partitioned between EtOAc (200 mL) and sat aq $NaHCO_3$ (250 mL) and the aqueous layer was extracted with EtOAc (5×100 mL). The combined organic fractions were concentrated in vacuo and the residue was purified by normal phase column chromatography to give the title compound (7.52 g, 31%) as a colourless gum. This process was repeated with 2.00 g Intermediate 1, and the products were combined and purified by reverse phase column chromatography to give the title compound (11.5 g, 39.5%) as a colourless gum. LCMS (ES+): 401.0 [MH]+. HPLC: Rt 3.91 min, 99.7% purity.

Biological Tests
In Vitro SSAO Enzyme Inhibition Assays

The in vitro SSAO enzyme inhibition assay was performed at room temperature with purified recombinantly expressed human SSAO. Enzyme was prepared essentially as described in Öhman et al. (Protein Expression and Purification 46 (2006) 321 331). The enzyme activity was assayed with benzylamine as substrate by measuring the production of hydrogen peroxide in a horseradish peroxidase (HRP) coupled reaction. Briefly, the test compound was dissolved in dimethyl sulfoxide (DMSO) to a concentration of 10 mM. Dose-response measurements were assayed by either creating 1:10 serial dilutions in DMSO to produce a 7 point curve or by making 1:3 serial dilutions in DMSO to produce 11 point curves. The top concentration was adjusted depending on the potency of the compound and subsequent dilution in reaction buffer yielded a final DMSO concentration 2%.

In a horseradish peroxidase (HRP) coupled reaction, hydrogen peroxide oxidation of 10-acetyl-3,7-dihydroxyphenoxazine produced resorufin, which is a highly fluorescent compound (Zhout and Panchuk-Voloshina. Analytical Biochemistry 253 (1997) 169-174; Amplex® Red Hydrogen Peroxide/peroxidase Assay kit, Invitrogen A22188). Enzyme and test compound in 50 mM sodium phosphate, pH 7.4 were set to pre-incubate in flat-bottomed microtiter plates for approximately 15 min before initiating the reaction by addition of a mixture of HRP, benzylamine and Amplex reagent. Benzylamine concentration was fixed at a concentration corresponding to the Michaelis constant, determined using standard procedures. Fluorescence intensity was then measured at several time points during 1-2 h, exciting at 544 nm and reading the emission at 590 nm. The final concentrations of the reagents in the assay wells were: SSAO enzyme 1 ug/ml, benzylamine 100 uM, Amplex reagent 20 uM, HRP 0.1 U/mL and varying concentrations of test compound. The inhibition was measured as % decrease of the signal compared to a control without inhibitor (only diluted DMSO). The background signal from a sample containing no SSAO enzyme was subtracted from all data points. Data was fitted to a four parameter logistic model and an $IC_{50}$ value was calculated using the GraphPad Prism 4 or XLfit 4 programs.

Study 1

Effect of Example 1 in the Established Mouse Collagen-Induced Arthritis Model

Figure 1:
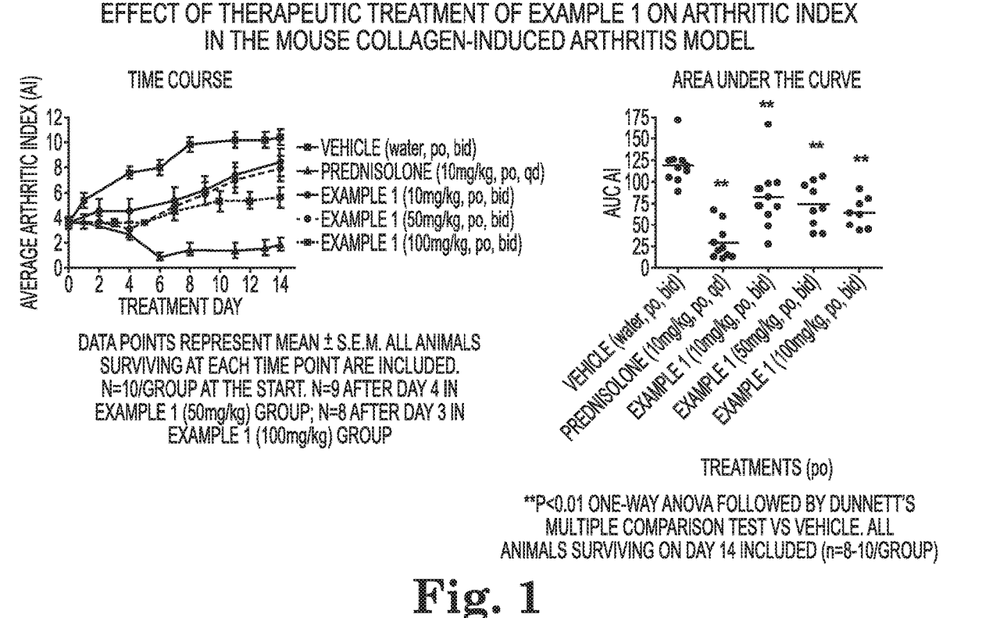
FIG. 1: Effect of {4-[3-(Dimethylamino)propoxy]phenyl}methyl (4S)-4-(propan-2-yl)-3H,4H,5H,6H,7H-imidazo[4,5-c]pyridine-5-carboxylate (referred to herein as Example 1) on Arthritic Index in the Collagen-Induced Arthritis Mouse Model. Data shows a dose-dependent decrease in the rate of disease development.

Example 1 was assessed in an established mouse collagen-induced arthritis model. Disease was induced in male DBA/1J mice by means of a subcutaneous injection of a collagen (bovine)/CFA emulsion at the base of the tail. Each paw was scored daily and the sum of all four scores was recorded as the Arthritic Index (AI). The maximum possible AI was 16 (0=no visible effects of arthritis, 1=edema and/or erythema of one digit, 2=edema and/or erythema of 2 joints, 3=edema and/or erythema of more than 2 joints, 4=severe arthritis of the entire paw and digits including limb deformation and ankylosis of the joint). As animals developed disease, they were sorted into treatment groups with AI in the range of 2-6 and an average group AI of 3.6 prior to initiation of the dosing regimen. Example 1 (10, 50 and 100 mg/kg) was administered orally twice daily from day 30 post-inoculation. The treatment resulted in a dose-dependent decrease in the rate of disease development such that at the termination of the study after two weeks of therapy the highest dose (100 mg/kg) had yielded a 46% reduction in disease severity (FIG. 1).

Figure 2:
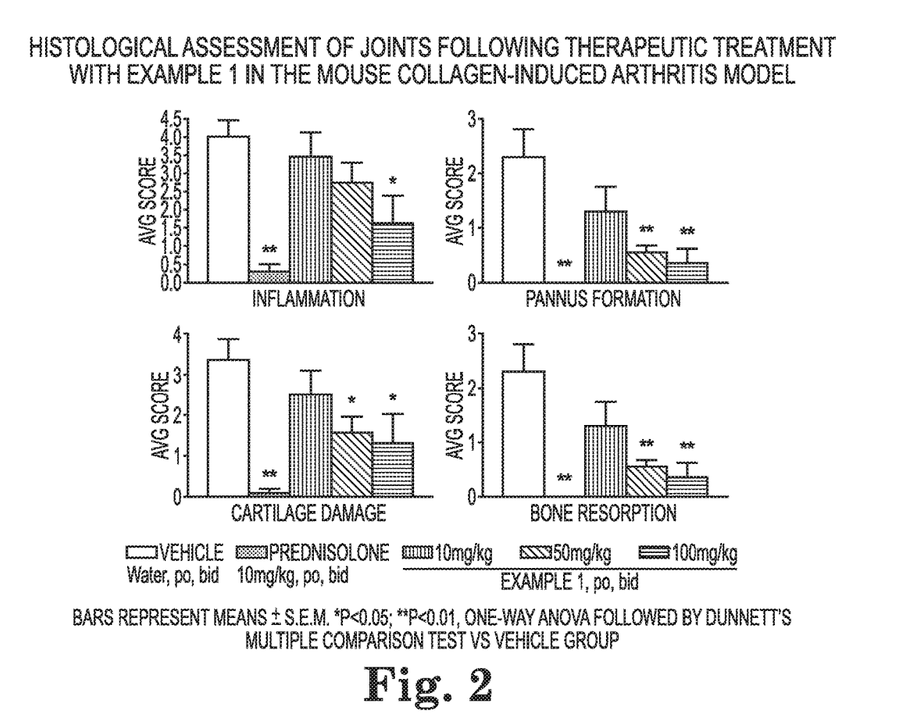
FIG. 2: Histological assessment of joints following treatment with Example 1 in the Collagen-Induced Arthritis Mouse Model. Data shows a dose-dependent inhibition of inflammation, pannus formation, cartilage damage, and bone resorption.

Histological evaluation of the rear right hind limbs was also carried out. The joints were scored for severity of arthritis (inflammation, pannus, cartilage damage and bone damage) by a board certified pathologist, who was blind to the assigned treatment. Assessment of the effect of Example 1 revealed a dose-dependent effect of the joints such that at the highest dose (100 mg/kg) a significant inhibition of inflammation (60%), pannus formation (84%), cartilage damage (60%), and bone resorption (84%) was recorded (FIG. 2).

Study 2

Effect of Example 1 in the DSS Mouse Colitis Model

Example 1 was assessed in the treatment of established disease in the chronic Dextran Sulphate (DSS)-induced colitis model. DSS was administered in the drinking water as a 3% solution for five days. DSS-treated mice were orally administered vehicle, 6-Thioguanine (0.5 mg/kg) or Example 1 (10 mg/kg, 30 mg/kg or 100 mg/kg) b.i.d. from Days 6 to 19. A no treatment control group of 5 mice was also used. Body weights were measured daily for 19 days and animals were assessed visually for the presence of diarrhea and/or bloody stool. All animals underwent video endoscopy on Days 5 (baseline), 12 and 19 to assess the extent of colitis and whether any beneficial treatment effects could be observed. All animals were euthanized on Day 19 to obtain colon tissues for pathology examination.

Figure 3:
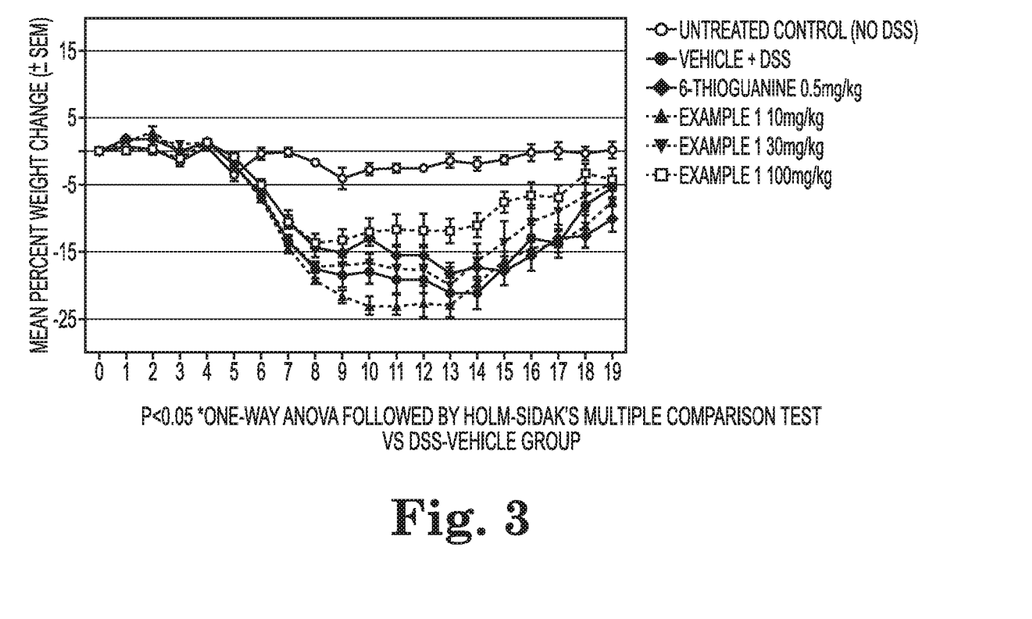
FIGS. 3-6: Effect of Example 1 in the DSS-Induced Colitis Mouse Model. Data shows a dose-dependent improvement in the DSS colitis model, with the dose of 100 mg/kg reaching statistically significant effects on overall body weight (FIG. 3), endoscopy scores on day 12 (FIG. 4), colon weight (FIG. 5) and diarrhea (FIG. 6).
Figure 4:
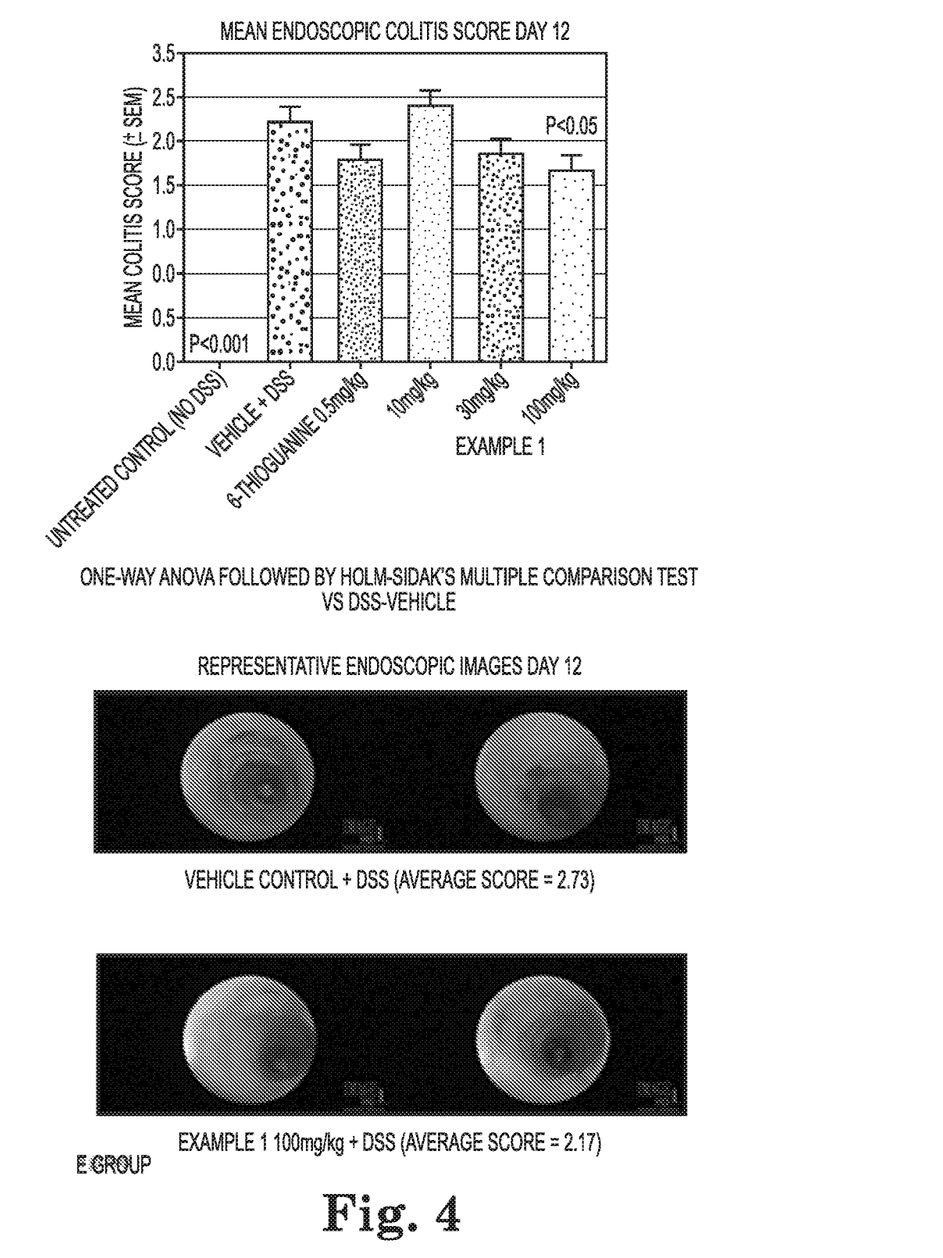
Figure 5:
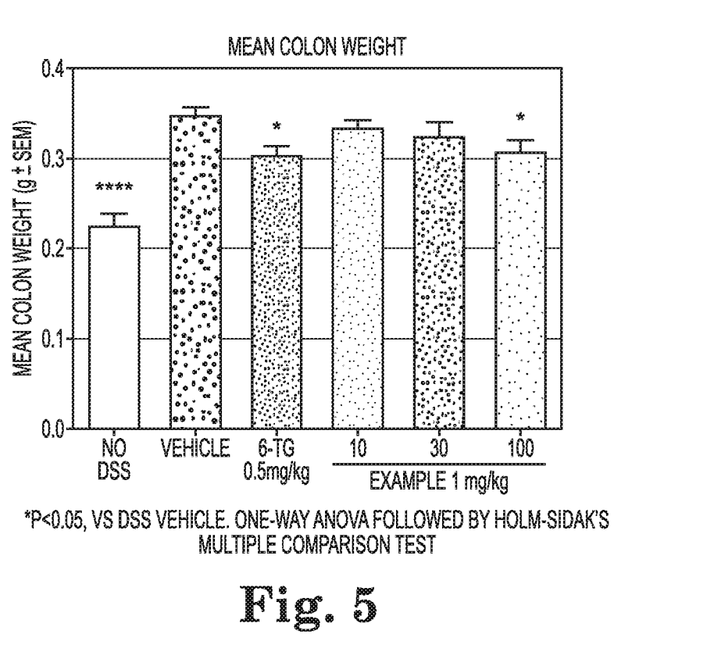
Figure 6:
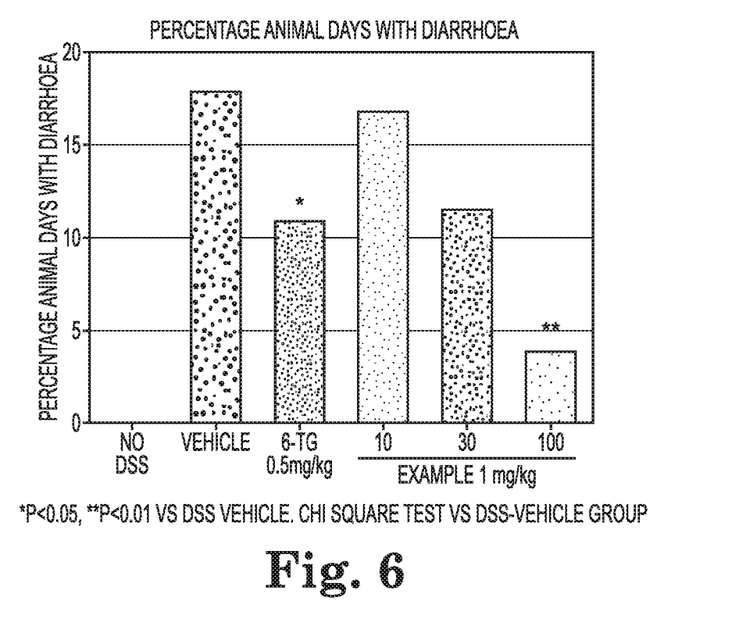

The therapeutic administration of Example 1 resulted in a dose-dependent improvement in the DSS colitis model, with the dose of 100 mg/kg reaching statistically significant effects on overall body weight (FIG. 3), endoscopy scores on day 12 (FIG. 4), colon weight (FIG. 5) and diarrhea (FIG. 6). The magnitude of the effect at this dose was comparable to the effect seen with the positive control, 6-Thioguanine.

Study 3

Effect of Example 1 in the Mouse PLP Relapsing-Remitting EAE Model

Example 1 was assessed in a $PLP_{139-151}$ remitting and relapsing model of experimental allergic encephalomyelitis (EAE) in female SJL mice as an indicator of a potential treatment for multiple sclerosis in humans.

Adjuvant was prepared by homogenizing 100 mg *Mycobacterium tuberculosis* H37 RA in 50 mL Incomplete Freund's Adjuvant to prepare a 2 mg/mL suspension which was stored at 4-8° C. 50 ug pertussis toxin from *Bordetella pertussis* was reconstituted in 50 mL sterile PBS to prepare a 1 ug/mL solution which was kept in an ice bath. 10.35 mg $PLP_{139-151}$ was dissolved in 10.35 mL sterile PBS to prepare a 1 mg/mL solution. 10 mL of $PLP_{139-151}$ was emulsified with 10 mL adjuvant in ten batches in an ice bath to prepare a 0.5 mg/mL $PLP_{139-151}$/1 mg/mL *M. tuberculosis* H37 RA emulsion which was kept in an ice bath. A drop of the emulsion was floated on water and did not disperse. On day 0, 70 mice were injected subcutaneously in both flanks with 0.1 mL of the $PLP_{139-151}$/CFA emulsion. Two hours later the mice were injected by intraperitoneal route with 0.2 mL pertussis toxin (200 ng/mouse). The mice were returned to routine maintenance with no adverse effects. On day 2, the mice were injected IP with 0.2 mL of pertussis toxin (200 ng/mouse). From day 7 the mice were weighed and scored for signs of disease as follows: 0=no obvious signs of motor dysfunction compared to non-immunized control; 1=limp or floppy tail; 2=limp tail and weakness in hind legs; 3=limp tail and complete paralysis of legs or limp tail with paralysis of one front and one hind leg; 4=limp tail, complete hind leg and partial front leg paralysis; 5=complete hind and complete front leg paralysis. On days 10-12, the mice were sorted into treatment groups based upon average score and twice daily oral administration of Example 1 (3, 10, 30 or 100 mg/kg), dexamethasone or vehicle (n=10 per group) was initiated. The disease score was monitored for 20 days.

Figure 7:
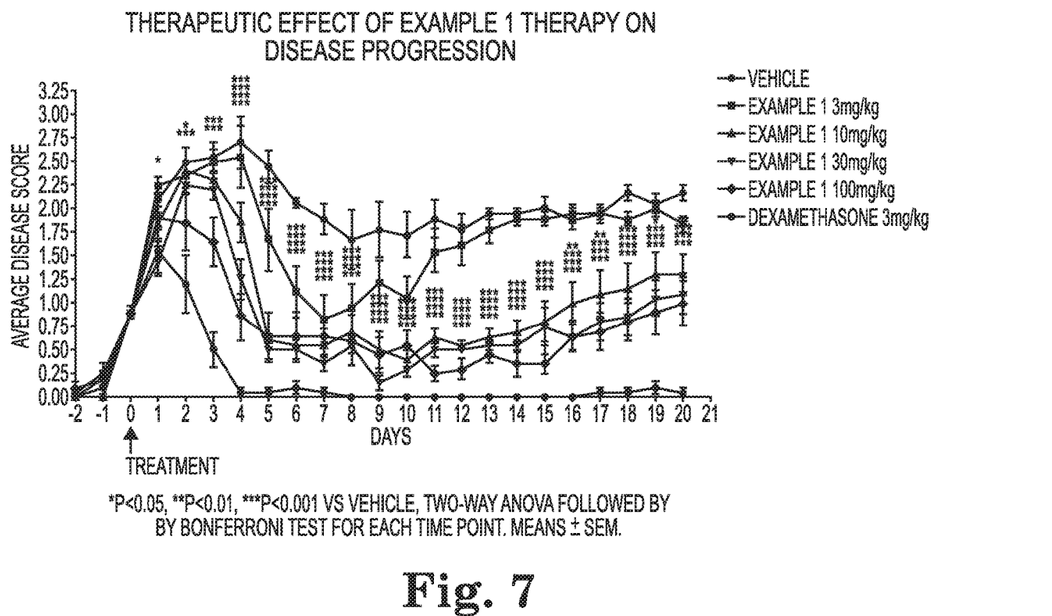
FIG. 7: Effect of Example 1 in the mouse PLP relapsing-remitting EAE model. Data shows a dose-dependent decrease in the time to disease remission, increased time to disease relapse and decrease in disease severity.

Twice daily therapeutic oral therapy with Example 1 resulted in a dose-dependent decrease in the time to disease remission, increased time to disease relapse and decrease in disease severity (in FIG. 7, day 0 has been re-set as the onset of therapy).

Study 4

Effect of Example 1 in a Carbon Tetrachloride Induced Liver Fibrosis Model

Example 1 was assessed in a carbon tetrachloride ($CCl_4$)-induced Liver Fibrosis Model. 7 week old female C57BL/6 mice were divided into four groups (n=5/group for one Control group to act as non-disease comparator and n=10/group for three $CCl_4$-treated groups based on their body weight the day before the start of the treatment. Thirty mice were intraperitoneally administered 5% $CCl_4$ in mineral oil at a volume of 100 uL twice a week (days 0, 4, 11, 14, 18, 21 and 25). Five mice intraperitoneally administered mineral oil instead of the 5% $CCl_4$, served as the non-diseased control group. Example 1 (100 mg/kg bid), Valsartan (20 mg/kg qd, positive control) and Vehicle were administered orally (dose volume=10 mL/kg) for 28 days (days −1 to 27). Mice in all groups were sacrificed after 16-20 hours from last dosing. Bouin's fixed left lateral liver sections were stained using picro-Sirius red solution. For quantitative analysis of fibrosis area, bright field images of Sirius red-stained section was blindly captured using a digital camera at 100-fold magnification, and the Sirius red-stained positive areas in 5 fields/4 um section/mouse were measured using ImageJ software (National Institute of Health, USA) and in accordance with the following expression: (collagen area/total area-vascular lumen area)×100. The operator was blinded to treatments. Statistical analyses were performed using one-way ANOVA followed by Bonferroni multiple comparison test on GraphPad Prism 4 (GraphPad Software, USA). P values <0.05 were considered statistically significant. A trend or tendency was assumed when a one-tailed t-test returned P values <0.10. Results were expressed as mean±SD. Comparison of the Valsartan group and Vehicle group in fibrosis area was assessed with student's t-test to confirm whether Valsartan worked as a positive control.

Figure 8:
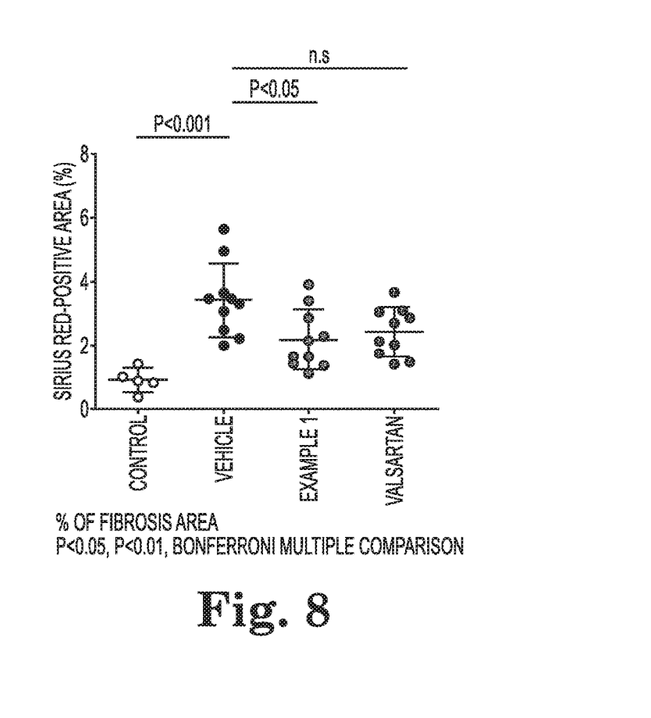
FIG. 8: Effect of Example 1 in a carbon tetrachloride induced Liver Fibrosis Model. Data shows treatment with Example 1 significantly reduced the deposition of collagen in the liver.

Treatment with Example 1 significantly reduced the deposition of collagen in the liver as demonstrated by Sirius red staining and thereby showed anti-fibrosis efficacy (see FIG. 8).

Study 5
Effect of Example 1 in a Murine Model of LPS-Induced Cytokine Release

Example 1 was assessed in an LPS-induced cytokine release assay. One hour after administration of Example 1, female Swiss Webster mice (n=5 per group) were injected intraperitoneally with 2 mL/kg LPS (1.5 mg/mL). One hour after LPS injection the mice were anesthetized and exsanguinated into pre-chilled serum separator microtainer tubes. The blood was processed to serum which was stored at −80° C. The frozen serum aliquots were thawed to room temperature, diluted 1:5 with sterile saline and assayed by ELISA for TNFα.

Figure 9:
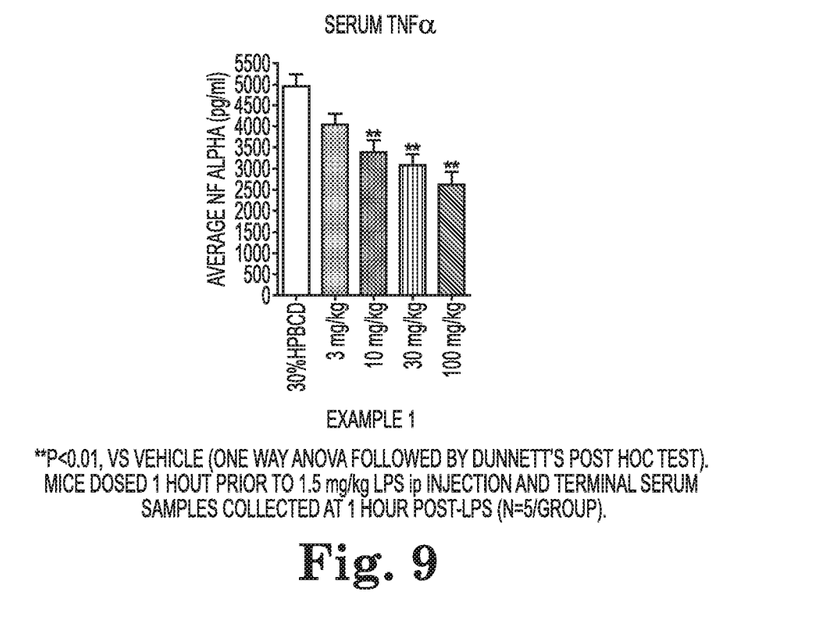
FIG. 9: Effect of Example 1 in a murine model of LPS-induced cytokine release. Data shows a statistically significant dose-dependent decrease in serum TNFα levels.

Oral administration of Example 1 one hour prior to LPS challenge resulted in a statistically significant dose-dependent decrease in serum TNFα levels, relative to the vehicle control (Group 1) (see FIG. 9).

Study 6
Effect of Example 1 in the Mouse Choroidal Neovascularisation Model

Figure 10:
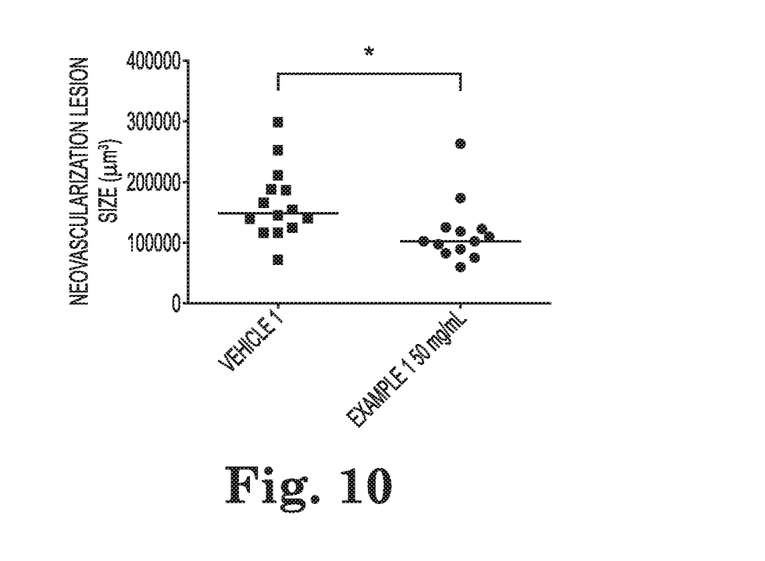
FIG. 10: Effect of Example 1 in the mouse choroidal neovascularisation model. Data shows a significant reduction in lesion size.

Example 1 was assessed in a mouse choroidal neovascularisation model. Pigmented mice (C57BL6 strain, n=15 per group) each were induced with 3 choroidal burns in the right eyes using a 532 nm photocoagulator. Example 1 and vehicle were dosed topically using 5 uL instillations tid from days 0 to 12. On day 12, lesion size was determined by isolectine B4 immunostaining on flatmount choroids from the treated eyes and confocal microscopy for determining the size of the lesion. Example 1 showed a significant reduction in lesion size versus vehicle treated animals (see FIG. 10).

Study 7
Effect of Example 1 in a Murine Model of Duchenne's Muscular Dystrophy

C57BL/10ScSn-$D_{mdx}$/J male mice were dosed from 27 days for 4 weeks with either vehicle (n=5), prednisolone (1 mg/kg ip qd, n=8) or Example 1 (100 mg/kg po bid, n=8). At 8 weeks of age, blood was collected by retro-orbital bleeding, and mice were humanely euthanized by $CO_2$ asphyxiation. One triceps surae was collected fresh and processed for immune cell sorting, one tibialis anterior was preserved in RNALater for RNA extraction, one whole hind limb and the diaphragm were fixed in 2% paraformaldehyde overnight at 4° C. for paraffin embedding and histology stains. Serum was prepared immediately after collection and frozen at −20° C. At the end of the study, all serum samples were dosed for Creatine Kinase on a Beckman Coulter AU Clinical Chemistry analyzer following manufacturer instructions (a modification of the International Federation of Clinical Chemistry method).

For immune cell sorting, muscle samples were enzymatically and mechanically dissociated following manufacturer instructions (Skeletal Muscle Dissociation KitCatalog no. 130-098-305, Miltenyi Biotec). Cells were stained with the following antibodies:

| Antigen | Clone | Cell type (for illustration purposes) |
| --- | --- | --- |
| CD4 (L3/T4) | GKL5 | T helper |
| CD8a | 53-6.72 | T Cytotoxic |
| CD11b/MAC-1 | M1/70 | Monocytes |
| GR-1/Ly6G | RB6-8C | Neutrophils |
| CD45R (B220) | RA3-6B2 | Leukocytes |
| Ly6C | AL-21 | Pro-/anti-inflammatory monocytes |

Stained cells were analyzed on a BD LSR II cytometer and counts of different populations were expressed in percentage of the number of live cells counted. Total RNAs were extracted with a modification of the Trizol method, reverse transcribed, and mRNAs of TGFα, and the following inflammation markers were quantified by the SYBR green method with GAPDH as a normalizer:

| mRNA | Cell type/event |
| --- | --- |
| TNFα | Pro-inflammatory cytokine |
| Interleukin 6 | Pro-inflammatory cytokine |
| Mpeg1 | Macrophage |
| Lgals3 | Macrophage |
| CD53 | B/T cells |
| CD48 | B/T cells activation |
| Ly6c | Pro-/anti-inflammatory monocytes |
| CD11b/MAC-1 | Monocytes |

Figure 11:
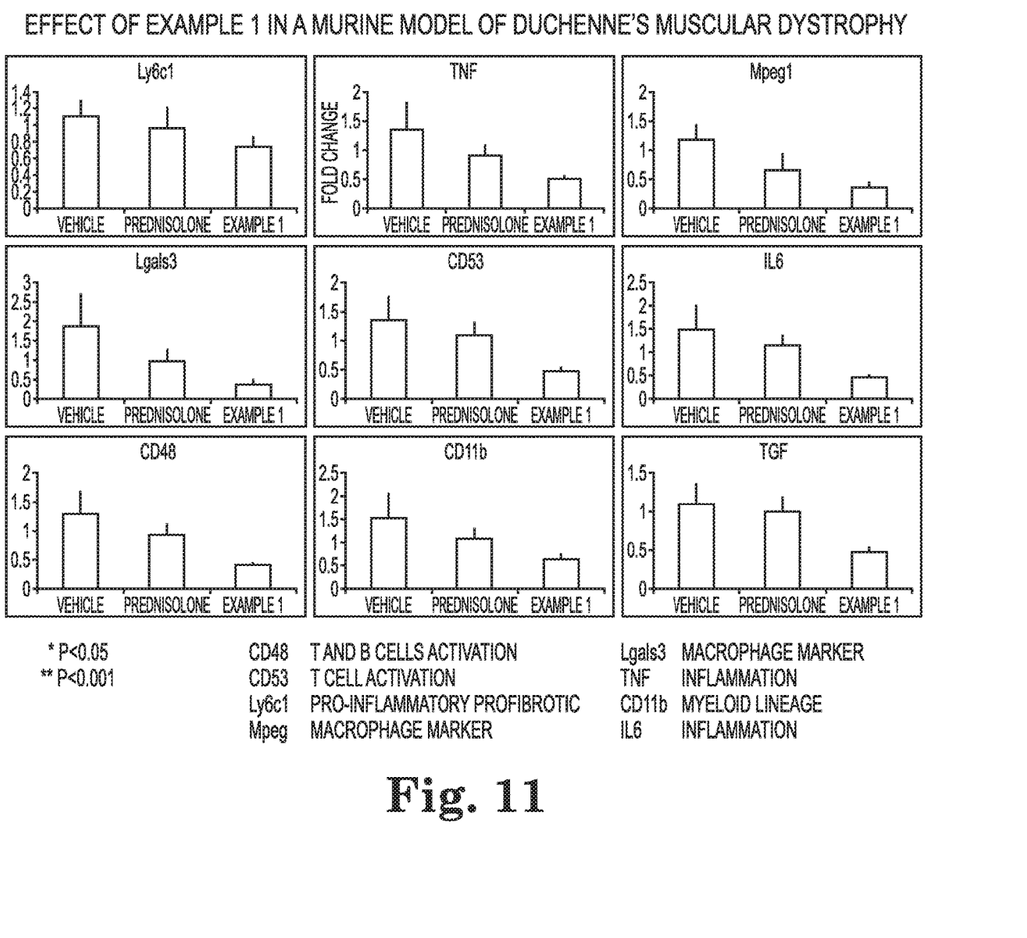
FIG. 11: Effect of Example 1 in a murine model of Duchenne's muscular dystrophy. Data shows a significant reduction in pro-inflammatory monocytes, cytokines, macrophages, B cells, T cells and TGFβ in mdx mice.

Example 1 showed a significant reduction in pro-inflammatory monocytes, cytokines, macrophages, B cells, T cells and TGFβ in the mdx mice (see FIG. 11).

The invention claimed is:

1. {4-[3-(Dimethylamino)propoxy]phenyl}methyl (4S)-4-(propan-2-yl)-3H,4H,5H,6H,7H-imidazo[4,5-c]pyridine-5-carboxylate, and pharmaceutically or veterinarily acceptable salts thereof.

2. A pharmaceutical composition comprising {4-[3-(Dimethylamino)propoxy]phenyl}methyl (4S)-4-(propan-2-yl)-3H,4H, 5H,6H, 7H-imidazo[4,5-c]pyridine-5-carboxylate or a pharmaceutically acceptable salt thereof, and one or more suitable excipients.

3. A veterinary composition comprising {4-[3-(Dimethylamino)propoxy]phenyl}methyl (4S)-4-(propan-2-yl)-3H, 4H, 5H,6H, 7H-imidazo[4,5-c]pyridine-5-carboxylate or a veterinarily acceptable salt thereof, and one or more suitable excipients.

* * * * *